US012426881B2

(12) United States Patent
Du et al.

(10) Patent No.: US 12,426,881 B2
(45) Date of Patent: Sep. 30, 2025

(54) POWERED ACTUATION ASSIST FOR AN OPEN LINEAR STAPLING DEVICE (71) Applicant: Covidien LP, Mansfield, MA (US)

(72) Inventors: Fen Du, Shanghai (CN); Hui Zhan, Shanghai (CN); Sridharan Varadhan, Shanghai (CN)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 18/294,662

(22) PCT Filed: Aug. 4, 2021

(86) PCT No.: PCT/CN2021/110466
§ 371 (c)(1),
(2) Date: Feb. 2, 2024

(87) PCT Pub. No.: WO2023/010314
PCT Pub. Date: Feb. 9, 2023

(65) Prior Publication Data
US 2025/0221708 A1    Jul. 10, 2025

(51) Int. Cl.
A61B 17/072    (2006.01)
A61B 17/00    (2006.01)

(52) U.S. Cl.
CPC ............. A61B 17/07207 (2013.01); A61B 2017/00398 (2013.01); A61B 2017/00477 (2013.01);
(Continued)

(58) Field of Classification Search
CPC ................................ A61B 17/07207
See application file for complete search history.

(56) References Cited

U.S. PATENT DOCUMENTS 7,721,933 B2 *    5/2010 Ehrenfels ......... A61B 17/07207
227/176.1
2004/0232200 A1    11/2004 Shelton et al.
(Continued)

FOREIGN PATENT DOCUMENTS

CN    106456166 A    2/2017
CN    107405172 A    11/2017
(Continued)

OTHER PUBLICATIONS

International Search Report dated Apr. 28, 2022, issued in corresponding international application No. PCT/CN2021/110466, 3 pages.
(Continued)

Primary Examiner — Nathaniel C Chukwurah (57) ABSTRACT

A surgical kit includes a stapling device and a powered actuation assist detachably couplable to the stapling device. The stapling device includes an anvil half section, a cartridge receiving half section, and a firing assembly including an actuation knob movable along a length of the cartridge receiving half section. The powered actuation assist includes a motor assembly, a lead screw operatively coupled to the motor assembly, a knob connector coupled to the lead screw, a battery pack, and a first switch electrically coupled to the motor to activate the motor. The knob connector is configured to detachably engage the actuation knob of the stapling device to impart axial displacement to the actuation knob. Actuation of the motor assembly imparts rotation to the lead screw, which, in turn, causes axial displacement of the actuation knob of the firing assembly.

20 Claims, 10 Drawing Sheets (52) U.S. Cl.
CPC ............ *A61B 2017/00734* (2013.01); *A61B 2017/07257* (2013.01); *A61B 2017/07271* (2013.01)

(56) References Cited

U.S. PATENT DOCUMENTS

| | | | |
|---|---|---|---|
| 2007/0125828 A1* | 6/2007 | Rethy | A61B 17/105 227/176.1 |
| 2019/0046193 A1* | 2/2019 | Dunki-Jacobs | A61B 17/0686 |

FOREIGN PATENT DOCUMENTS

| | | |
|---|---|---|
| CN | 110381851 A | 10/2019 |
| CN | 111801055 A | 10/2020 |
| CN | 112584778 A | 3/2021 |
| EP | 3061410 A1 | 8/2016 |
| WO | 2022/233036 A1 | 11/2022 |

OTHER PUBLICATIONS

European Search Report for EP Application No. 21952217.4 mailed Mar. 17, 2025 (8 pages).

* cited by examiner

POWERED ACTUATION ASSIST FOR AN OPEN LINEAR STAPLING DEVICE

TECHNICAL FIELD

The disclosure relates to a surgical stapling device and, more particularly, to a powered actuation assist for use with an open linear stapling device.

BACKGROUND

Surgical stapling devices for dispensing staples to suture tissue during surgical procedures are well known. Linear type surgical stapling devices typically include a tool assembly having jaws that are movable in relation to each other between spaced and clamped positions. The jaws have proximal ends that are pivotally coupled to each other and distal ends that are spaced longitudinally from their proximal ends. The tool assembly includes a staple cartridge that houses a plurality of staples and a firing mechanism that translates from a proximal end of the tool assembly to a distal end of the tool assembly to sequentially eject staples from the staple cartridge. The jaws of the tool assembly are supported at their proximal ends in cantilevered fashion.

A continuing need exists in the art for providing improved staple formation along the entire length of the tool assembly.

SUMMARY

The disclosure describes a powered actuation assist for use with an open linear stapling device that demonstrates a practical approach to meeting the performance requirements and overcoming usability challenges associated with actuating an open linear stapling device during a surgical procedure.

In accordance with the disclosure, a surgical kit includes a stapling device and a powered actuation assist detachably couplable to the stapling device. The stapling device includes an anvil half section, a cartridge receiving half section including a staple cartridge, and a firing assembly including an actuation knob movable along a length of the cartridge receiving half section to eject staples from the staple cartridge. The anvil half section and the cartridge receiving half section are transitionable between clamped and unclamped configurations. The powered actuation assist includes a motor assembly, a lead screw operatively coupled to the motor assembly, a knob connector coupled to the lead screw such that rotation of the lead screw causes axial displacement of the knob connector, a battery pack electrically coupled to the motor assembly to supply power thereto, and a first switch electrically coupled to the motor to activate the motor. The knob connector is configured to detachably engage the actuation knob of the stapling device to impart axial displacement to the actuation knob. Actuation of the motor assembly imparts rotation to the lead screw, which, in turn, causes axial displacement of the actuation knob of the firing assembly.

In an aspect, the powered actuation assist may further include a coupling arm including first and second portions and a connecting portion interconnecting the first and second portions. The first and second portions may define respective first and second recesses to secure the stapling device thereto.

In another aspect, the first recess may receive a first protruding portion of the cartridge receiving half section of the stapling device, and the second recess may receive a second protruding portion of the anvil half section of the stapling device.

In yet another aspect, the second portion may further include a cutout that is configured to slidably receive the second protruding portion of the anvil half section of the stapling device.

In still yet another aspect, the knob connector of the powered actuation assist may include first and second segments defining a gap to receive the actuation knob of the stapling device.

In still yet another aspect, the knob connector may further include a coupling ring interconnecting the first and second segments. The coupling ring may be configured to receive the lead screw of the powered actuation assist.

In an aspect, the lead screw may include a threaded portion and the coupling ring may have a pin configured to engage the threaded portion of the lead screw.

In another aspect, the knob connector may include a guide that inhibits rotation of the knob connector, whereby rotation of the lead screw causes axial displacement of the knob connector.

In yet another aspect, the powered actuation assist may further include a printed circuit board and first and second buttons coupled to the printed circuit board. The first and second buttons may activate the motor to provide rotation of the lead screw in opposite directions.

In an aspect, the powered actuation assist may include a housing having proximal portion, a body portion, and a distal portion. The proximal portion may include a case defining a first chamber configured to receive the motor assembly. The body may define a second chamber configured to receive the lead screw. The distal portion may define a third chamber configured to receive the battery pack.

In another aspect, the case may be detachably coupled to the body portion.

In accordance with another aspect of the disclosure, a powered actuation assist for use with an open linear stapling device includes an actuation assembly, a battery pack electrically coupled to a motor assembly of the actuation assembly to supply power thereto, and a coupling assembly. The actuation assembly includes the motor assembly and a lead screw operatively coupled to the motor assembly. The coupling assembly includes a knob connector operatively supported on the lead screw such that rotation of the lead screw causes axial displacement of the knob connector. The knob connector is configured to provide axial input to an actuation assembly of the open linear stapling device.

In an aspect, the coupling assembly may further include a coupling arm including first and second portions defining respective first and second recesses to receive portions of the open linear stapling device.

In another aspect, the powered actuation assist may further include a switch electrically coupled to the motor assembly.

In yet another aspect, the switch may include first and second buttons to activate the motor assembly to cause axial displacement of the knob connector in opposite directions.

In still yet another aspect, the knob connector may further include first and second segments defining gap therebetween.

In an aspect, the knob connector may further include a coupling ring interconnecting the first and second segments. The coupling ring may be configured to receive the lead screw therethrough.

In an aspect, the coupling ring may further include a pin configured to engage a threaded portion of the lead screw.

In another aspect, the actuation assembly may include a case detachably covering the motor assembly.

In still yet another aspect, the knob connector may further include a guide that inhibits rotation of the knob connector about the lead screw.

BRIEF DESCRIPTION OF DRAWINGS

The above and other aspects and features of this disclosure will become more apparent in view of the following detailed description when taken in conjunction with the accompanying drawings wherein like reference numerals identify similar or identical elements.

DETAILED DESCRIPTION

The powered actuation assist disclosed herein is described in detail with reference to the drawings, in which like reference numerals designate identical or corresponding elements in each of the several views. As used herein, the term "distal" refers to the portion that is being described which is farther from a user during use of the device in its customary fashion, while the term "proximal" refers to the portion that is being described which is closer to a user during use of the device in its customary fashion. In addition, the terms parallel and perpendicular are understood to include relative configurations that are substantially parallel and substantially perpendicular up to about + or −10 degrees from true parallel and true perpendicular. Further, to the extent consistent, any or all of the aspects detailed herein may be used in conjunction with any or all of the other aspects detailed herein.

Figure 1:
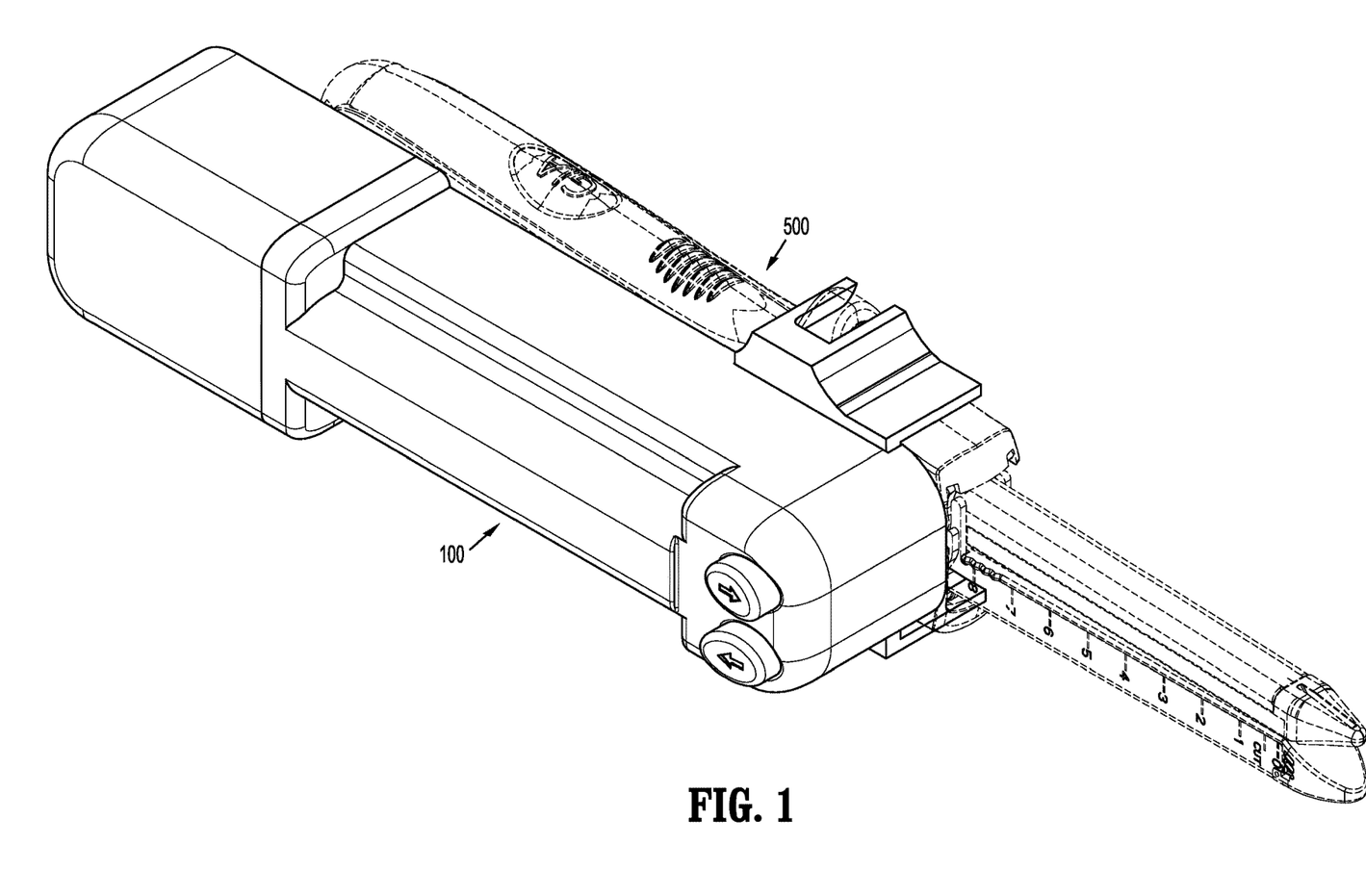
FIG. 1 is a perspective view of a powered actuation assist in accordance with the disclosure, illustrating use with a stapling device.

FIG. 1 illustrates a powered actuation assist 100 for use with a stapling device 500 in a form of an open linear stapling device in accordance with the disclosure. The powered actuation assist 100 is detachably couplable to the stapling device 500. The powered actuation assist 100 may be operatively coupled to the stapling device 500 to provide an axial input for actuation of the stapling device 500. Specifically, the powered actuation assist 100 imparts axial displacement to an actuation knob 522 (FIG. 2) of the stapling device 500 to eject staples from a cartridge assembly or a single use loading unit 518 of the stapling device 500, as will be described. In this manner, the powered actuation assist 100 provides uniform application of staples to tissue and reduces or eliminates user fatigue.

Figure 2:
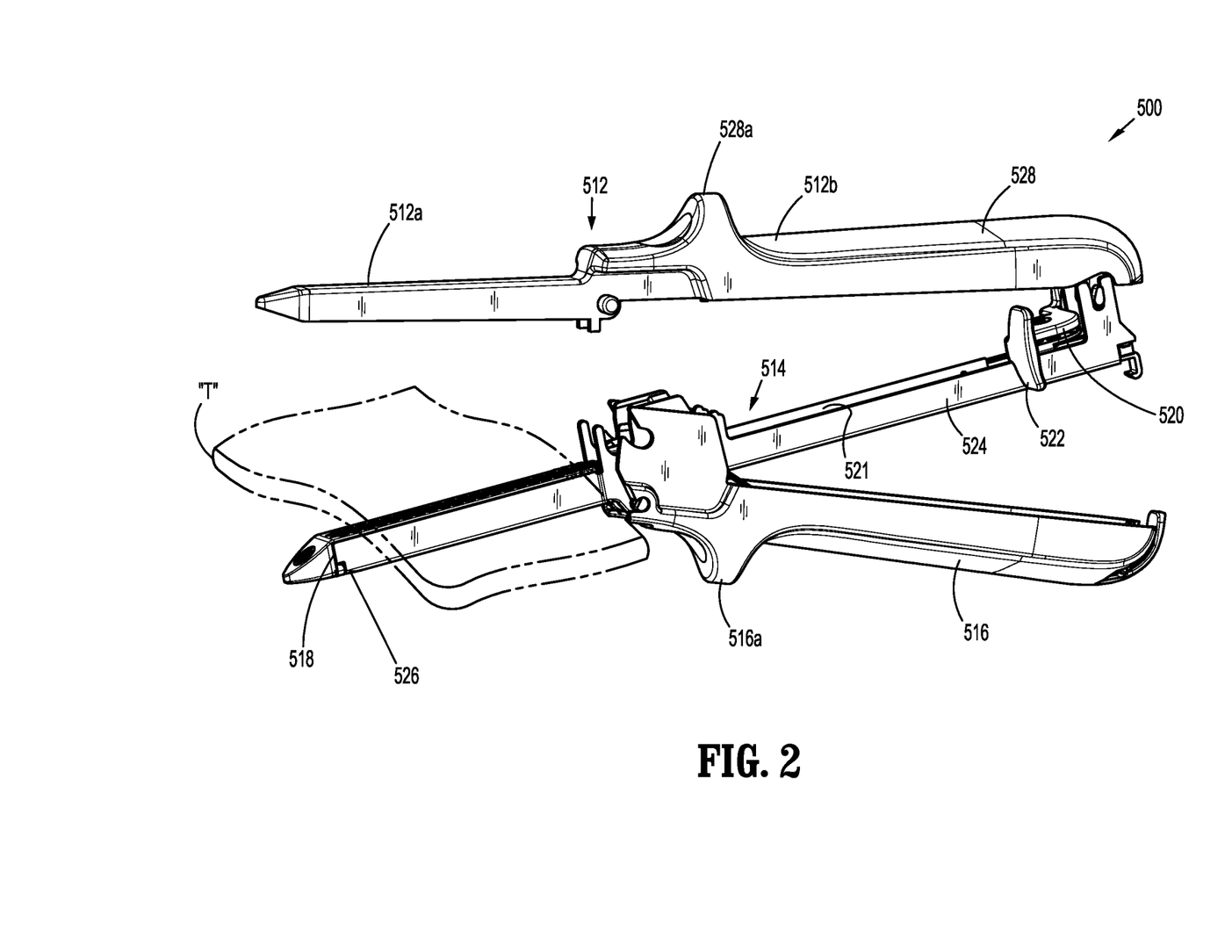
FIG. 2 is a perspective view of the stapling device of FIG. 1 in an unclamped configuration.

FIGS. 1 and 2 illustrate the stapling device 500 that includes an anvil half section 512, a cartridge receiving half section 514 supporting a clamping lever 516, a cartridge assembly or single use loading unit 518 (hereinafter "SULU"), and a firing assembly 520. The cartridge receiving half section 514 includes a channel member 521 having a proximal portion 524 and a distal portion 526. The proximal portion 524 of the channel member 521 receives the firing assembly 520 and pivotally supports the clamping lever 516. The distal portion 526 of the channel member 521 receives the SULU 518. The anvil half section 512 includes a distal portion 512a that supports an anvil (not shown) having a tissue contact surface and a proximal portion 512b that supports a hand grip 528. The tissue contact surface of the anvil defines a plurality of staple deforming recesses and is movable into opposition with the SULU 518 upon actuation of the clamping lever 516.

The clamping lever 516 is pivotally supported on the cartridge receiving half section 514 and is engageable with the anvil half section 512 such that movement of the clamping lever 516 from an unclamped position (FIG. 2) to a clamped position (FIG. 1) moves the anvil half section 12 into close approximation with the cartridge receiving half section 514. When tissue "T" is clamped between the anvil of the anvil half section 512 and the SULU 518 of the cartridge receiving half section 514, the firing assembly 520 may be actuated to eject staples from the SULU 518 to staple tissue "T". Detailed operation and construction of surgical stapling devices of similar construction are described in U.S. Pat. No. 8,505,801 ('801 patent) and U.S. Pat. No. 7,721,933 ('933 patent) which are incorporated herein by reference in their entirety.

Figure 3:
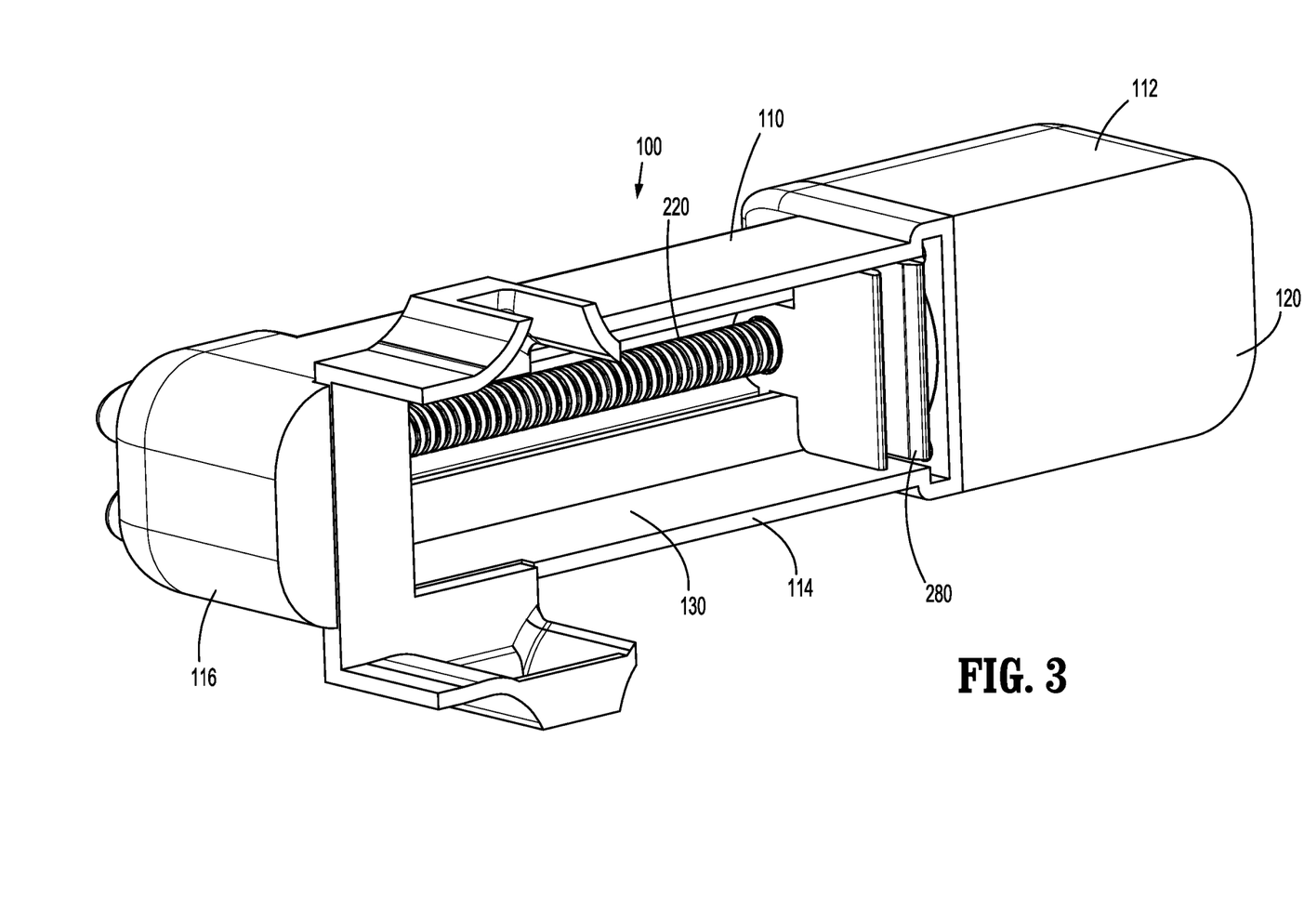
FIG. 3 is a perspective view of the powered actuation assist of FIG. 1.
Figure 4:
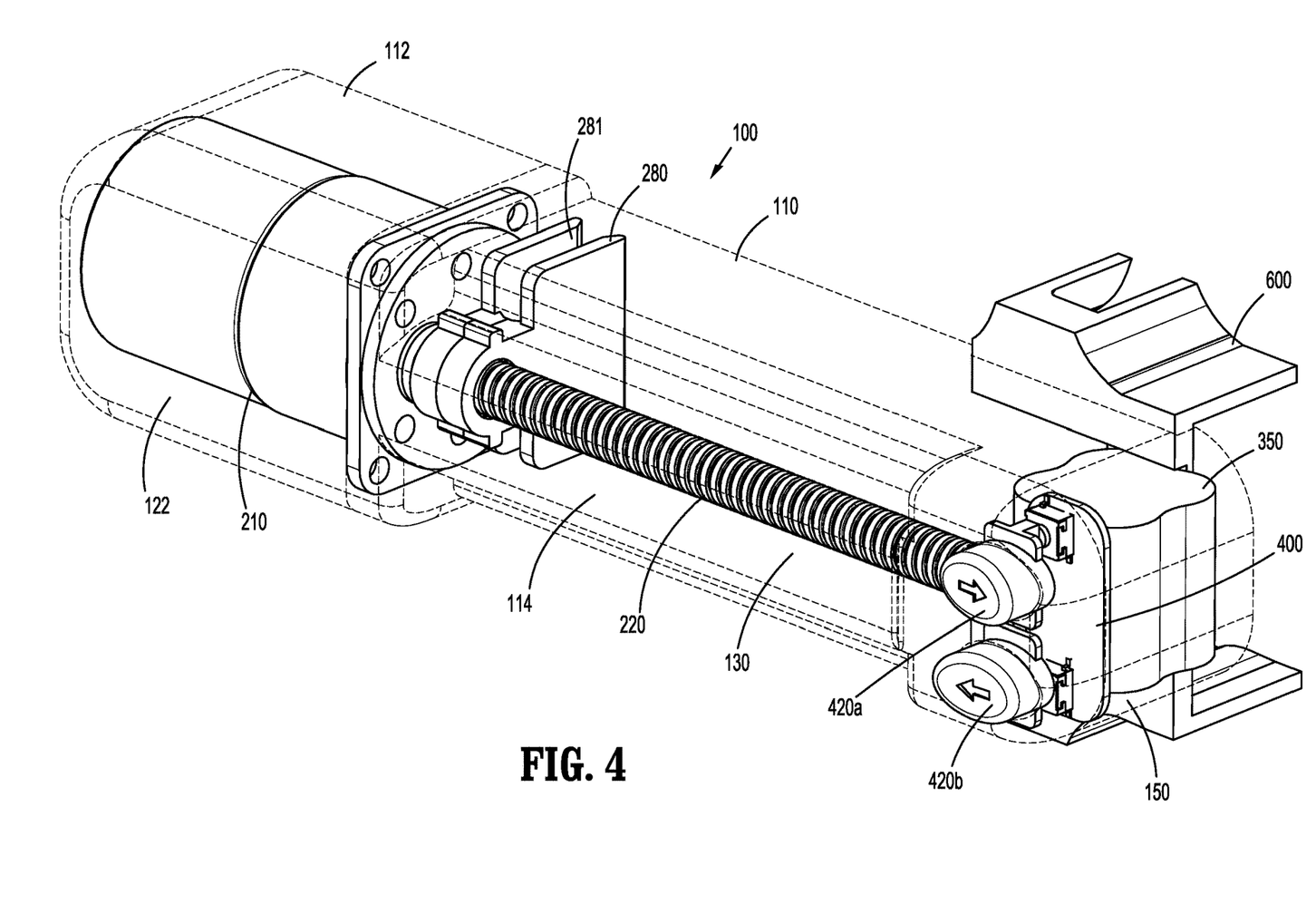
FIG. 4 is a perspective view of an actuation assembly of the powered actuation assist of FIG. 3.

Referring to FIGS. 3 and 4, the powered actuation assist 100 includes a housing 110 having a proximal portion 112, a body portion 114, and a distal portion 116. The proximal portion 112 includes a case 120 defining a first chamber 122, and the body portion 114 defines a second chamber 130. The distal portion 116 defines a third chamber 150. The case 120 may be detachably coupled to the body portion 114. The body portion 114 and the distal portion 116 may be monolithically formed as a single construct.

Figure 5:
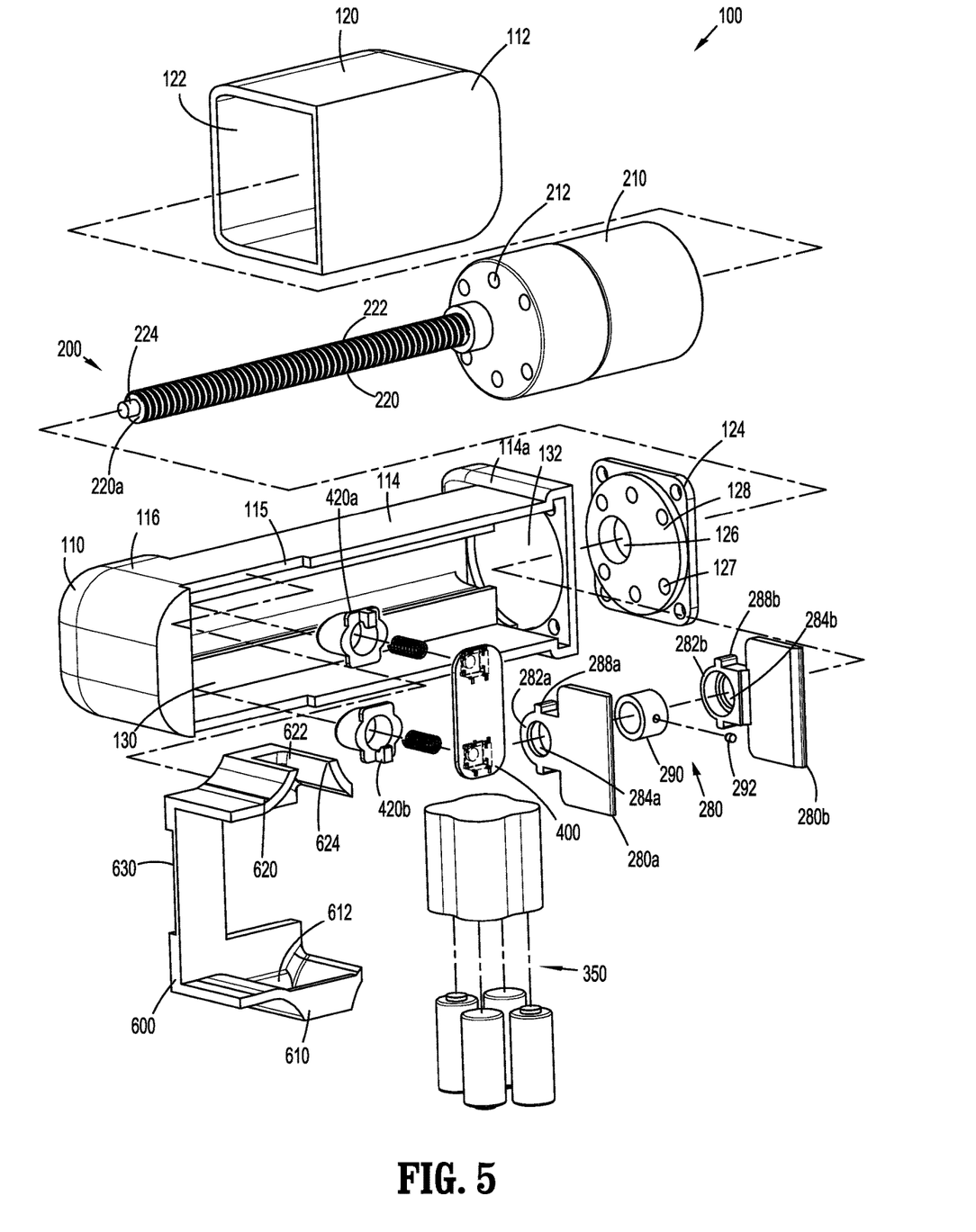
FIG. 5 is an exploded perspective view of the powered actuation assist of FIG. 1 with parts separated.

FIGS. 4 and 5 illustrate an actuation assembly 200 of the powered actuation assist 100. The actuation assembly 200 includes a motor assembly 210 and a lead screw 220 operatively coupled to the motor assembly 210. The motor assembly 210 has a cylindrical body including a motor and a gearbox to provide a desired output of torque and/or speed. The motor assembly 210 is received in the first chamber 122 of the case 120 that is detachably coupled to the body portion 114 of the housing 110. In particular, the case 120 includes a cover 124 defining a bore 126 dimensioned to receive the lead screw 220 therethrough. In an aspect, the cover 124 may include a circular protrusion 128 that is configured to be received in an opening 132 defined in a proximal portion 114a of the body portion 114 of the housing 110 and secured thereto via, e.g., friction fit. The circular protrusion 128 further defines a plurality of through holes 127 that are in registration with holes 212 defined in the motor assembly 210. In an aspect, screws may be utilized to secure the motor assembly 210 to the cover 124 of the case 120. In addition, the cover 124 may be secured to the body portion 114 of the housing 110 via, e.g., screws. The case 120 is detachably coupled to the cover 124. In an aspect, the cover 124 is received in the first chamber 122 and removably secured thereto via, e.g., friction fit. The lead screw 220 extends through the bore 126 of the cover 124 and is rotatably disposed in the second chamber 130 of the body portion 114. The lead screw 220 includes a threaded portion 222 and a distal tip 224 at a distal portion 220a of the threaded portion 222. The distal tip 224 is rotatably supported in the distal portion 116 of the housing 110 such that when the motor assembly 210 is activated, the motor imparts rotation to the lead screw 220. The actuation assembly 200 further includes a knob connector 280 configured to receive the actuation knob 522 (FIG. 2) of the stapling device 500 to impart axial displacement to the actuation knob 522.

Figure 6:
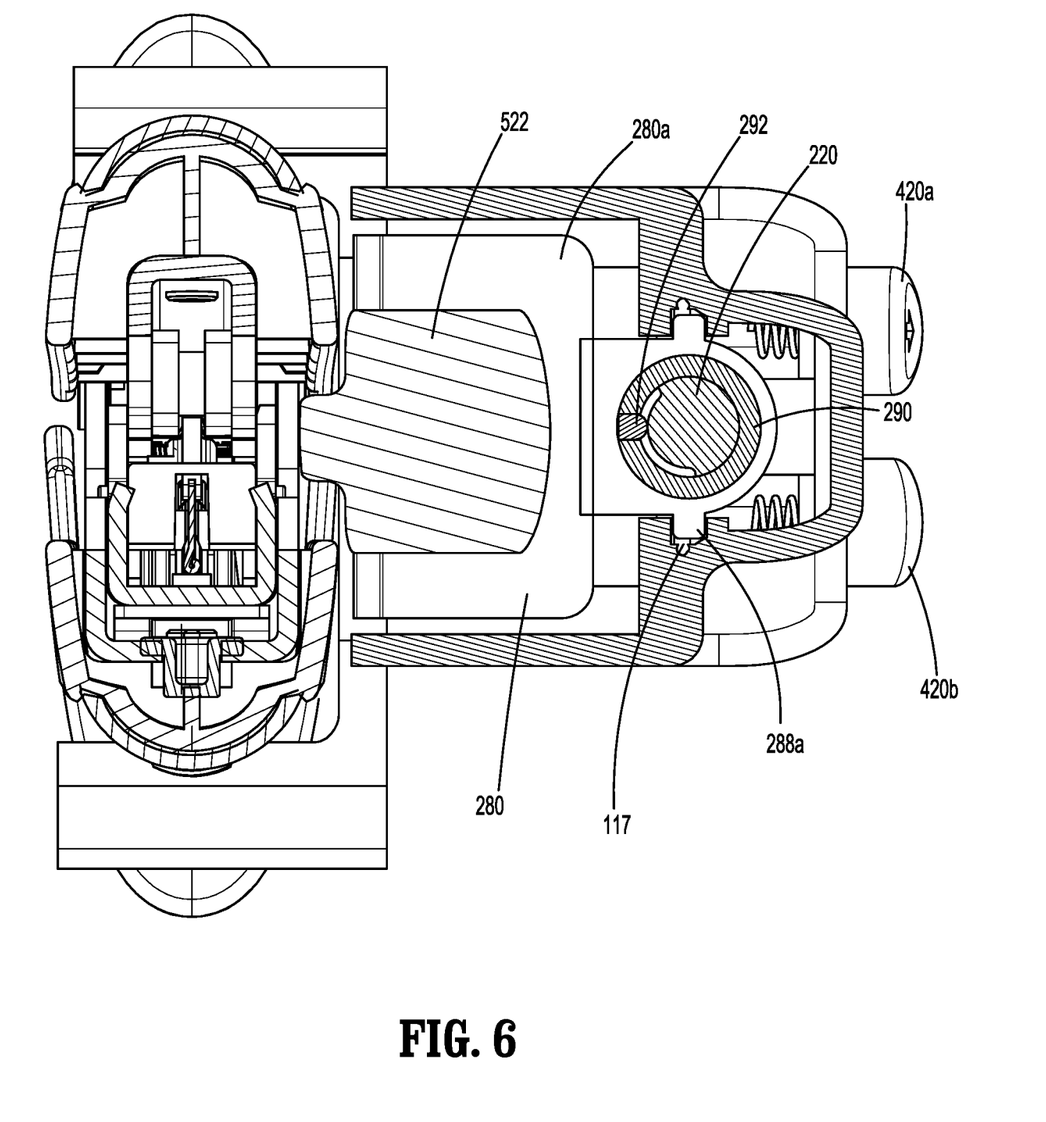
FIG. 6 is a cross-sectional view of the powered actuation assist and the stapling device of FIG. 1.

As shown in FIGS. 5 and 6, the knob connector 280 includes first and second sections 280a, 280b and a coupling ring 290. The first and second sections 280a, 280b include respective coupling portions 282a, 282b defining bores 284a, 284b that are configured to receive the lead screw 220 therethrough. In addition, the coupling portions 282a, 282b include respective guides 288a, 288b that are configured to cammingly be received within grooves 117 (FIG. 6) defined in the housing 110 to inhibit rotation of the knob connector 280 and facilitate axial displacement of the knob connector 280. The coupling ring 290 is at least partially received and secured with the respective coupling portions 282a, 282b of the first and second sections 280a, 280b. The first and second sections 280a, 280b define a gap 281 (FIG. 7) therebetween. The coupling ring 290 is configured to receive the lead screw 220 therethrough. In particular, the coupling ring 290 has a pin 292 that engages threads on the threaded portion 222 of the lead screw 220. Under such a configuration, rotation of the lead screw 220 advances or retracts the knob connector 280 along the lead screw 220.

FIGS. 4 and 5 further illustrate the third chamber 150 of the distal portion 116 of the housing 110. The third chamber 150 supports a battery pack 350 and a printed circuit board 400 that is electrically coupled to the battery pack 350 and to the motor assembly 210. The printed circuit board 400 is also coupled to actuation buttons 420a, 420b to activate the motor assembly 210. The actuation buttons 420a, 420b are configured activate the motor assembly 210 to rotate the lead screw 220 in opposite directions in order to advance and retract the knob connector 280. The housing 110 has a coupling arm 600 attachable to the distal portion 116 of the housing 110. The coupling arm 600 has opposing first and second portions 610, 620 and a connecting portion 630 interconnecting the first and second portions 610, 620. The first portion 610 defines a recess 612 that is configured to receive a protruding portion 516a (FIG. 2) of the clamping lever 516 of the stapling device 500. The second portion 620 defines a recess 622 that receives a protruding portion 528a (FIG. 2) of the hand grip 528 of the anvil half section 512. The second portion 620 further defines a cutout 624 that receives the protruding portion 528a therethrough. The connecting portion 630 is secured to a cutout 115 of the housing 110.

Figure 7:
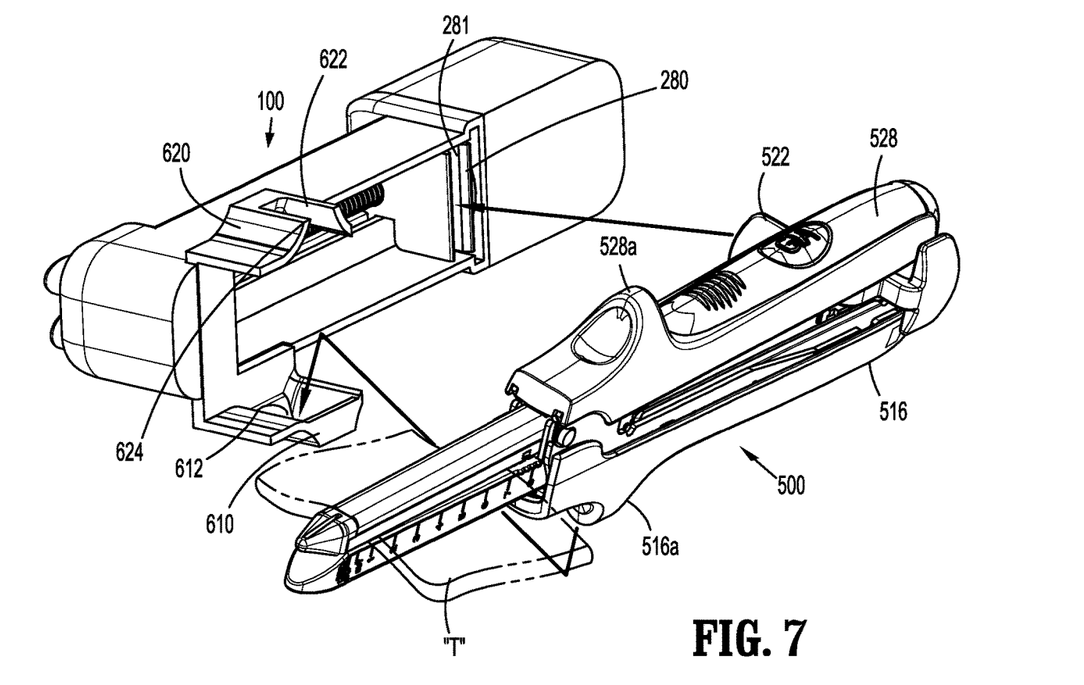
FIGS. 7-9 are perspective views of the powered actuation assist and the stapling device of FIG. 1, illustrating attachment of the powered actuation assist to the stapling device.
Figure 8:
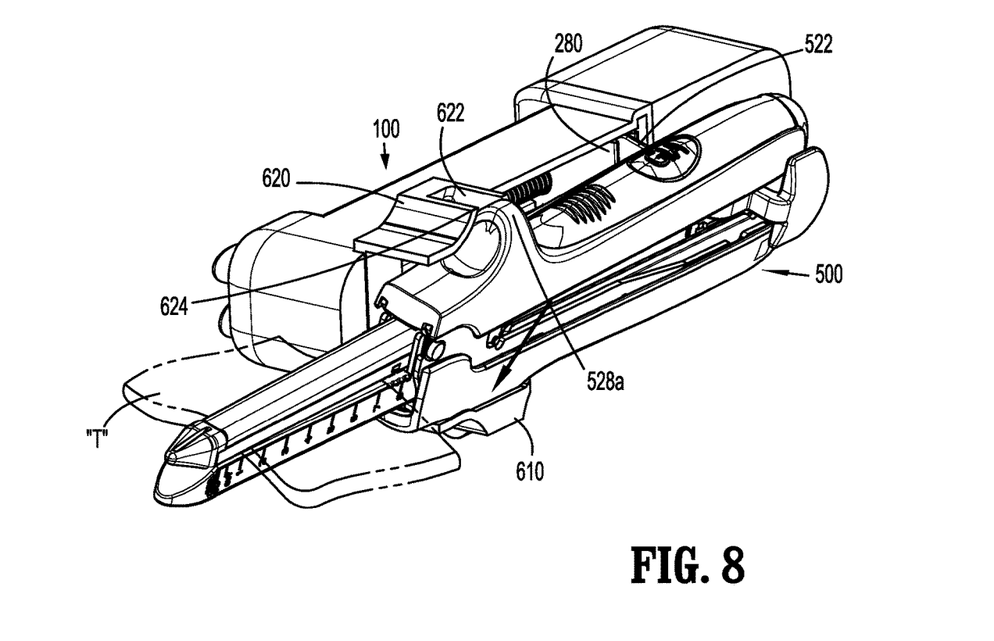
Figure 9:
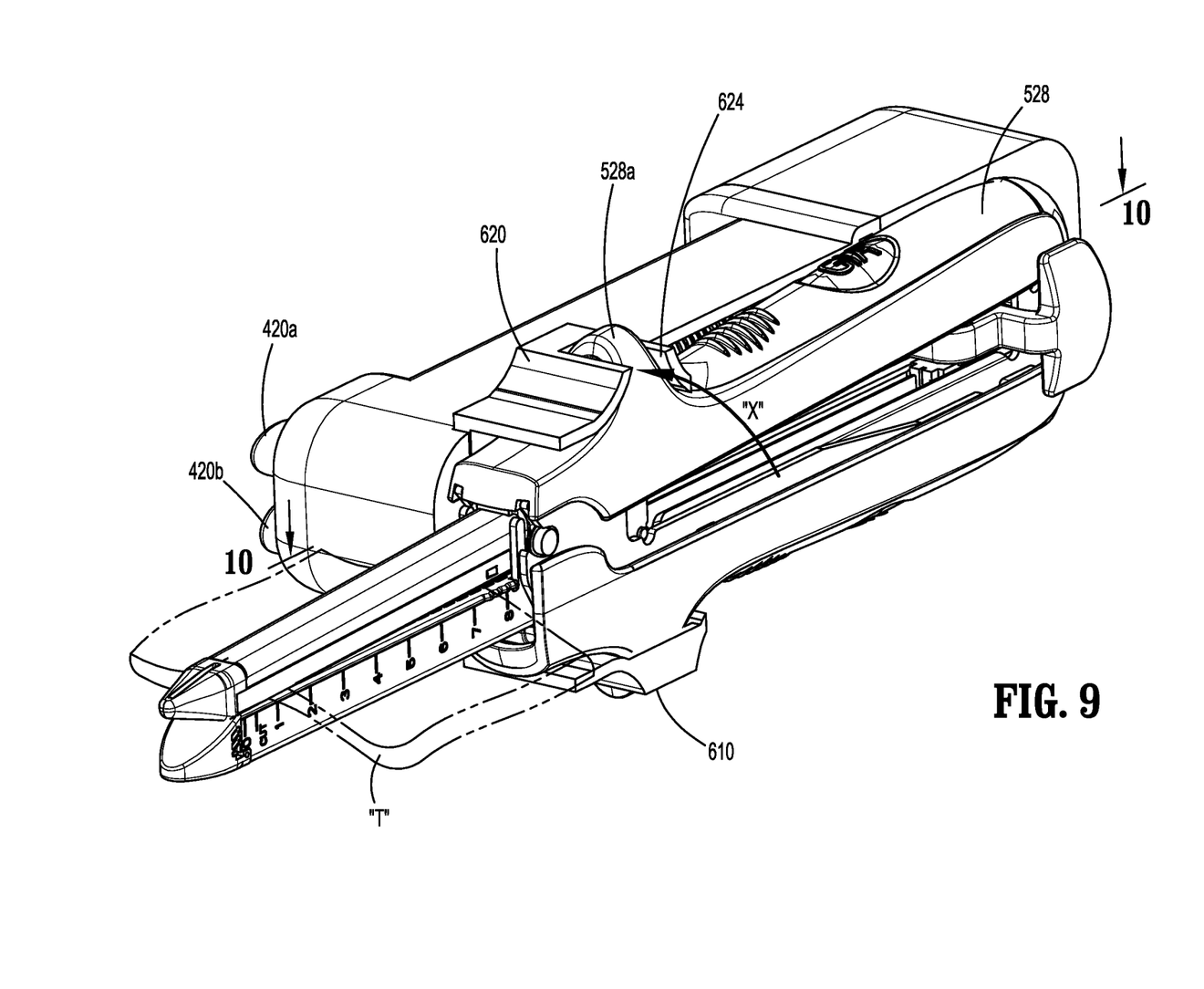

Initially, as shown in FIG. 2, the stapling device 500 receives tissue "T" between the anvil half section 512 and the cartridge receiving half section 514 in the unclamped configuration. Thereafter, the stapling device 500 is transitioned to the clamped configuration by approximating the hand grip 528 and the clamp lever 516 relative to each other, as shown in FIG. 7. After the stapling device 500 is clamped on tissue "T", the stapling device 500 is ready to be coupled to the powered actuation assist 100. As shown in FIGS. 7 and 8, the protruding portion 516a of the clamping lever 516 of the stapling device 500 is placed in the first recess 612 of the first portion 610 of the powered actuation assist 100, and the actuation knob 522 of the stapling device 500 is placed in the gap 281 of the knob connector 280 of the powered actuation assist 100. Thereafter, the protruding portion 528a of the hand grip 528 is received in the recess 622 of the second portion 620 in the direction of an arrow "X" (FIG. 9) through the cutout 624. In this manner, the actuation knob 522 is operatively coupled to the power actuation assist 100, as shown in FIG. 9.

Figure 10:
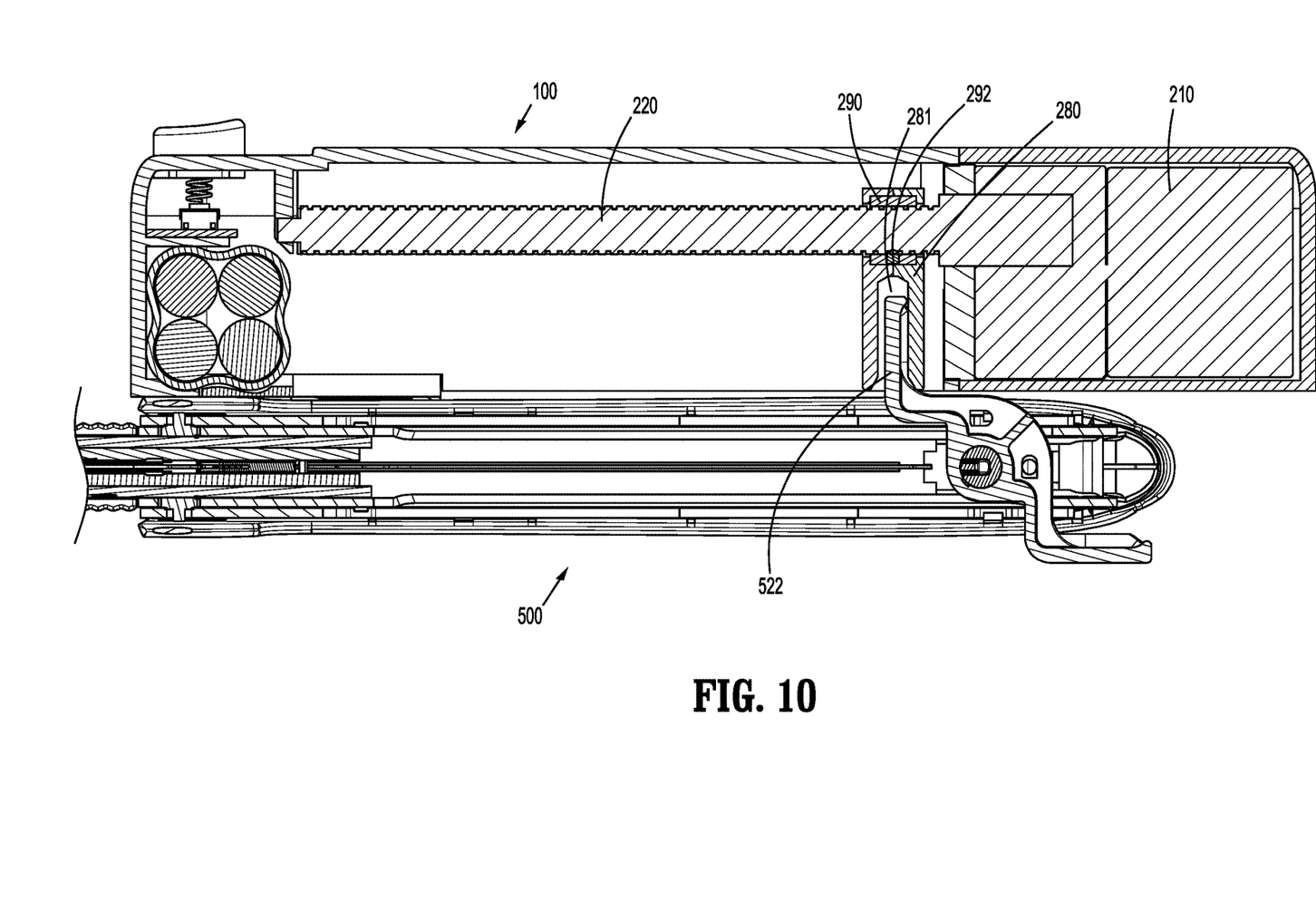
FIG. 10 is a side cross-sectional view taken along section line 10-10 of FIG. 9.
Figure 11:
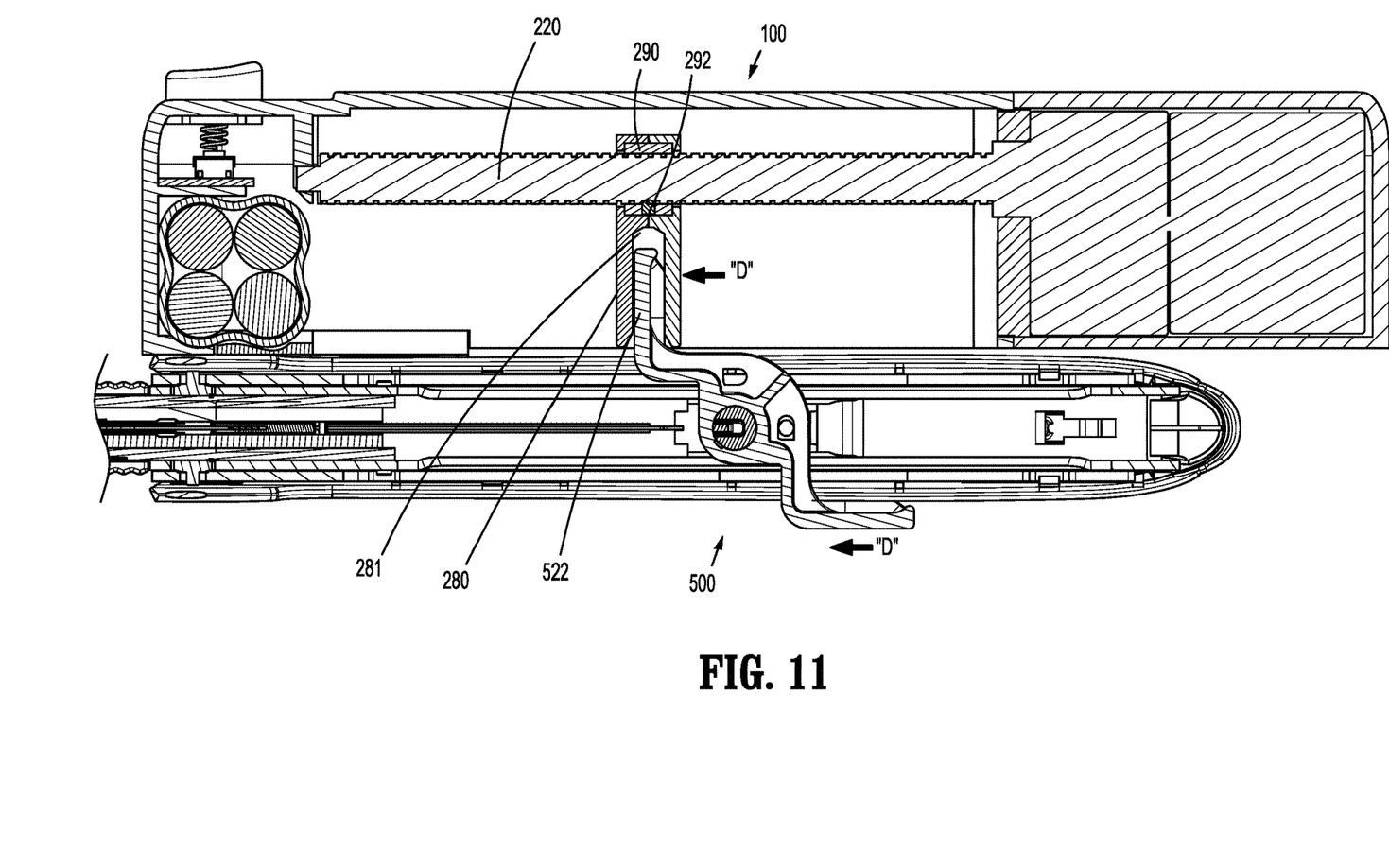
FIG. 11 is a partial side cross-sectional view of the powered actuation assist and the stapling device of FIG. 10, illustrating use thereof.

As shown in FIG. 10, prior to actuation, the actuation knob 522 of the stapling device 500 is in a proximal-most position. At this time, a clinician may depress the button 420a of the powered actuation assist 100, which, in turn, activates the motor assembly 210. Activation of the motor assembly 210 imparts rotation to the lead screw 220, which, in turn, advances the coupling ring 290 in the direction of arrows "D" (FIG. 11). In this manner, the actuation knob 522 is advanced by the knob connector 280, which, in turn, actuates the stapling device 500 to apply staples to tissue "T". After the staples are applied to tissue "T", the actuation knob 522 may be retracted by depressing the button 420b (FIG. 9) which activates the motor assembly to rotate the lead screw 220 in the opposite direction to retract the actuation knob 522.

While the disclosure has been shown in the drawings, it is not intended that the disclosure be limited thereto, as it is intended that the disclosure be as broad in scope as the art will allow and that the specification be read likewise. Therefore, the above description should not be construed as limiting, but merely as exemplifications. Those skilled in the art will envision other modifications within the scope and spirit of the claims appended hereto.

What is claimed is:

1. A surgical kit comprising:
 a stapling device including:
  an anvil half section;
  a cartridge receiving half section including a staple cartridge; and
  a firing assembly including an actuation knob movable along a length of the cartridge receiving half section to eject staples from the staple cartridge, the anvil half section and the cartridge receiving half section being transitionable between clamped and unclamped configurations; and
 a powered actuation assist detachably couplable to the stapling device, the powered actuation assist including:
  a motor assembly;
  a lead screw operatively coupled to the motor assembly;
  a knob connector coupled to the lead screw such that rotation of the lead screw causes axial displacement of the knob connector, the knob connector configured to detachably engage the actuation knob of the stapling device to impart axial displacement to the actuation knob;
  a battery pack electrically coupled to the motor assembly to supply power thereto; and
  a first switch electrically coupled to the motor to activate the motor,
 wherein actuation of the motor assembly imparts rotation to the lead screw, which, in turn, causes axial displacement of the actuation knob of the firing assembly.

2. The surgical kit according to claim 1, wherein the powered actuation assist further includes a coupling arm including first and second portions and a connecting portion interconnecting the first and second portions, the first and second portions defining respective first and second recesses to secure the stapling device thereto.

3. The surgical kit according to claim 2, wherein the first recess receives a first protruding portion of the cartridge receiving half section of the stapling device, and the second recess receives a second protruding portion of the anvil half section of the stapling device.

4. The surgical kit according to claim 3, wherein the second portion further includes a cutout that is configured to slidably receive the second protruding portion of the anvil half section of the stapling device.

5. The surgical kit according to claim 3, wherein the knob connector of the powered actuation assist includes first and second segments defining a gap to receive the actuation knob of the stapling device.

6. The surgical kit according to claim 5, wherein the knob connector further includes a coupling ring interconnecting the first and second segments, the coupling ring configured to receive the lead screw of the powered actuation assist.

7. The surgical kit according to claim 6, wherein the lead screw includes a threaded portion and the coupling ring has a pin configured to engage the threaded portion of the lead screw.

8. The surgical kit according to claim 1, wherein the knob connector includes a guide that inhibits rotation of the knob connector, whereby rotation of the lead screw causes axial displacement of the knob connector.

9. The surgical kit according to claim 1, wherein the powered actuation assist further includes a printed circuit board and first and second buttons coupled to the printed circuit board, the first and second buttons activates the motor to provide rotation of the lead screw in opposite directions.

10. The surgical kit according to claim 1, wherein the powered actuation assist includes a housing having proximal portion, a body portion, and a distal portion, the proximal portion including a case defining a first chamber configured to receive the motor assembly, the body defining a second chamber configured to receive the lead screw, and the distal portion defining a third chamber configured to receive the battery pack.

11. The surgical kit according to claim 10, wherein the case is detachably coupled to the body portion.

12. A powered actuation assist for use with an open linear stapling device comprising:
   an actuation assembly including:
      a motor assembly; and
      a lead screw operatively coupled to the motor assembly;
   a battery pack electrically coupled to the motor assembly to supply power thereto; and
   a coupling assembly including a knob connector operatively supported on the lead screw such that rotation of the lead screw causes axial displacement of the knob connector, the knob connector configured to provide axial input to an actuation assembly of the open linear stapling device.

13. The powered actuation assist according to claim 12, wherein the coupling assembly further includes a coupling arm including first and second portions defining respective first and second recesses to receive portions of the open linear stapling device.

14. The powered actuation assist according to claim 12, further comprising a switch electrically coupled to the motor assembly.

15. The powered actuation assist according to claim 14, wherein the switch includes first and second buttons to activate the motor assembly to cause axial displacement of the knob connector in opposite directions.

16. The powered actuation assist according to claim 12, wherein the knob connector includes first and second segments defining gap therebetween.

17. The powered actuation assist according to claim 16, wherein the knob connector further includes a coupling ring interconnecting the first and second segments, the coupling ring configured to receive the lead screw therethrough.

18. The powered actuation assist according to claim 17, wherein the coupling ring further includes a pin configured to engage a threaded portion of the lead screw.

19. The powered actuation assist according to claim 12, wherein the actuation assembly includes a case detachably covering the motor assembly.

20. The powered actuation assist according to claim 12, wherein the knob connector further includes a guide that inhibits rotation of the knob connector about the lead screw.

* * * * *